(12) United States Patent
McCullagh et al.

(10) Patent No.: US 7,402,170 B2
(45) Date of Patent: Jul. 22, 2008

(54) CRIMP AND WELD WIRE CONNECTION

(75) Inventors: Orla McCullagh, Watertown, MA (US); Robert Thistle, Bridgewater, MA (US)

(73) Assignee: Scimed Life Systems, Inc., Maple Grove, MN (US)

(*) Notice: Subject to any disclaimer, the term of this patent is extended or adjusted under 35 U.S.C. 154(b) by 480 days.

(21) Appl. No.: 10/748,444

(22) Filed: Dec. 30, 2003

(65) Prior Publication Data

US 2005/0149171 A1    Jul. 7, 2005

(51) Int. Cl.
*A61F 2/06* (2006.01)
(52) U.S. Cl. .................................... 623/1.16
(58) Field of Classification Search ............... 623/1.16
See application file for complete search history.

(56) References Cited

U.S. PATENT DOCUMENTS

| | | | |
|---|---|---|---|
| 4,655,771 A | 4/1987 | Wallsten | 623/1 |
| 5,061,275 A | 10/1991 | Wallsten et al. | 623/1 |
| 5,643,339 A | 7/1997 | Kavteladze et al. | 623/1.22 |
| 5,836,966 A | 11/1998 | St. Germain | 606/198 |
| 5,843,168 A | 12/1998 | Dang | 623/1 |
| 5,899,934 A | 5/1999 | Amundson et al. | 623/1 |
| 5,935,162 A | 8/1999 | Dang | 623/1 |
| 6,056,775 A | 5/2000 | Borghi et al. | 623/1.16 |
| 6,063,111 A | 5/2000 | Hieshima et al. | 623/1 |
| 6,139,573 A | 10/2000 | Sogard et al. | |
| 6,139,574 A | 10/2000 | Vacanti et al. | 623/1.44 |
| 6,146,403 A | 11/2000 | St. Germain | 606/198 |
| 6,214,025 B1 | 4/2001 | Thistle et al. | 606/200 |
| 6,224,626 B1 | 5/2001 | Steinke | 623/1.16 |
| 6,231,581 B1 | 5/2001 | Shank et al. | 606/157 |
| 6,264,689 B1 | 7/2001 | Colgan et al. | 623/1.22 |
| 6,355,059 B1 | 3/2002 | Richter et al. | 623/1.17 |
| 6,423,084 B1 | 7/2002 | St. Germain | 606/198 |
| 6,428,569 B1 | 8/2002 | Brown | 623/1.15 |
| 6,503,270 B1 | 1/2003 | Richter et al. | 623/1.15 |
| 6,589,275 B1 | 7/2003 | Ivancev et al. | 623/1.15 |
| 6,602,284 B2 | 8/2003 | Cox et al. | 623/1.15 |
| 6,616,689 B1 | 9/2003 | Ainsworth et al. | 623/1.16 |
| 6,626,935 B1 | 9/2003 | Ainsworth et al. | 623/1.15 |
| 6,635,083 B1 | 10/2003 | Cheng et al. | 623/1.15 |
| 6,660,034 B1 | 12/2003 | Mandrusov et al. | 623/1.42 |
| 2002/0029075 A1 | 3/2002 | Leonhardt | 623/1.11 |
| 2003/0139798 A1* | 7/2003 | Brown et al. | 623/1.15 |
| 2003/0195609 A1 | 10/2003 | Berenstein et al. | 623/1.15 |

* cited by examiner

*Primary Examiner*—Thomas J Sweet
(74) *Attorney, Agent, or Firm*—RatnerPrestia

(57) ABSTRACT

A stent comprises a first section and a second section and at least one securement member. The at least one securement member is disposed about at least one region of the first section and at least one region of the second section. The at least one securement member has a crimped diameter that is less than its uncrimped diameter. When the at least one securement member is in the crimped diameter at least a portion of an inner surface of the at least one securement member is fixedly engaged to the at least one region of the first section and the at least one region of the second section. In the crimped diameter the at least one region of the first section and the at least one region of the second section are immediately adjacent one another.

49 Claims, 11 Drawing Sheets

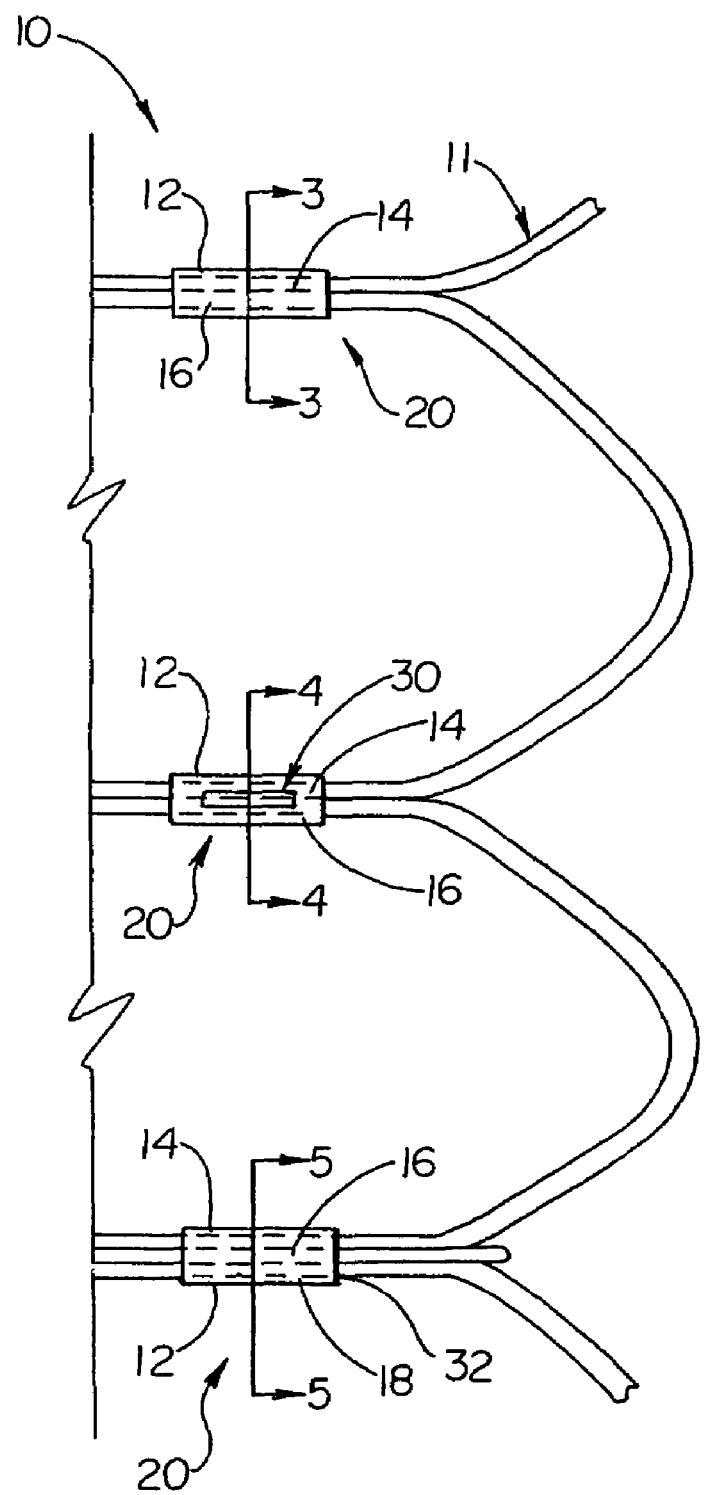

CRIMP AND WELD WIRE CONNECTION

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Stents, grafts, stent-grafts, vena cava filters and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, etc. Stents may be used to reinforce body vessels and to prevent restenosis following angioplasty in the vascular system. They may be self-expanding, mechanically expandable or hybrid expandable.

Stents are generally tubular devices for insertion into body lumens. However, it should be noted that stents may be provided in a wide variety of sizes and shapes. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents.

Stents may be constructed from a variety of materials such as stainless steel, Elgiloy, nickel, titanium, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired substantially tubular, bifurcated or other shape of the stent; one or more wires or ribbons of stent material may be woven, braided or otherwise formed into a desired shape and pattern. In some stents, one or more portions of the stent are welded together.

Some examples of stents or stent components that may be braided are described in U.S. Pat. No. 5,061,275, U.S. Pat. No. 4,655,771, U.S. Pat. No. 6,146,403, U.S. Pat. No. 5,836,966, U.S. Pat. No. 6,423,084, U.S. Pat. No. 6,139,573 as well as in U.S. application Ser. No. 10/063,315 to Eder et al., filed Apr. 10, 2002.

Typically, a stent is implanted in a blood vessel or other body lumen at the site of a stenosis or aneurysm by so-called "minimally invasive techniques" in which the stent is compressed radially inwards and is delivered by a catheter to the site where it is required through the patient's skin or by a "cut down" technique in which the blood vessel concerned is exposed by minor surgical means. When the stent is positioned at the correct location, the catheter is withdrawn and the stent is caused or allowed to expand to a predetermined diameter in the vessel.

Currently many stents, such as the prior art stent 100 shown in PRIOR ART FIG. 1, have one or more portions 102 and 104 that are secured together by a weld 106 at one or more points or seams where the portions are immediately adjacent one another. While stents having such welds 106 typically meet or exceed the performance requirements of clinical use, many perceive the welds 106 of such stents to be weak as the welds sometimes yield when subjected to handling. It is thus desirable to provide a mechanism for securing stent elements together which provides a stent with improved peel strength, improved shear or tensile strength, and/or improved radial strength at and/or around a securement site.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In light of the above the present invention is directed to a variety of embodiments. For example, in at least one embodiment the invention is directed to a stent having at least one securement member, which is disposed about two or more adjacent portions of a stent, in order to secure the portions together.

As indicated above a stent, or one or more portions thereof may be constructed to include different stent materials or configurations. As such, in some embodiments adjacent portions of the stent that are secured together by one or more securement members. Adjacent portions of the stent thusly secured may be comprised of one or more stent wire, struts and/or other members of a stent segment.

In at least one embodiment at least two adjacent portions of one or more members of a stent are secured together by one or more securement members. In some embodiments, at least three adjacent portions of one or more members are secured together by one or more securement members.

In at least one embodiment a securement member is a continuous band. In some embodiments a securement member is a strip of material coiled or wrapped around at least two adjacent portions of one or more members of a stent. In some embodiments the securement member is at least partially constructed of one or more metals, and/or polymers. In some embodiments the securement member is at least partially constructed of stainless steel, nickel, titanium, gold, platinum, and combinations and/or alloys thereof. In some embodiments the securement member is at least partially radiopaque. In some embodiments the securement member is at least partially constructed of nitinol. In some embodiments the securement member is at least partially coated with one or more polymers. In some embodiments the securement member is comprised of one or more layers of similar or different material.

In at least one embodiment a stent comprises a securement assembly, the securement assembly comprising at least two adjacent portions of the stent secured together with at least one securement member disposed thereabout. The securement assembly further comprising at least one weld connection wherein at least a portion of the crimping member and at least one of the at least two adjacent portions are fused or weldingly engaged together. In some embodiments the at least one weld connection comprises at least one spot weld, at least one seam weld, and/or a combination thereof.

In at least one embodiment the securement assembly further comprises at least one strengthening member. A strengthening member may be positioned at least partially between the at least two adjacent portions of the stent and the securement member. In some embodiments the at least one weld connection fuses one or more portions of the securement member, the strengthening member and the at least two adjacent portions of the stent together. In some embodiments the strengthening member extends beyond the length of the securement member over a region of the at least two adjacent portions of the stent. In some embodiments the length of the strengthening member that extends beyond the securement member is about 2.0 mm or more. In some embodiments the length of the strengthening member that is positioned between the at least two adjacent portions of the stent and the securement member is about 2.0 mm or more. In some embodiments the strengthening member is at least partially constructed of one or more metal and/or one or more polymer materials. In some embodiments the strengthening member is at least partially constructed of a nickel titanium alloy.

In at least one embodiment the securement member comprises an inner surface and an outer surface, the inner surface in at least partial contact with the portions of the stent secured therein. In some embodiments the inner surface defines at least one channel, wherein each portion of a stent contained within the securement member is positioned within a different channel.

In at least one embodiment the securement member has a predetermined thickness of about 0.001 inches to about 0.01 inches. In some embodiments the predetermined thickness is about 0.003 to about 0.007 inches.

In at least one embodiment the invention is directed to a system for securing adjacent segments of a stent wherein the system includes at least one securement member disposed about at least two portions of the adjacent segments and a crimping device for crimping the securement member to the at least two portions. In some embodiments the system includes a heating mechanism for selectively welding one or more regions of the securement member to one or more regions of the at least two portions at one or more locations.

In at least one embodiment the invention is directed to a method of securing adjacent segments of a stent together wherein a securement member is disposed about at least two portions of the adjacent segments and crimping the securement member to the at least two portions with a crimping device. In some embodiments the securement member is selectively welded or otherwise bonded to one or more regions of the at least two portions.

In at least one embodiment at least a portion of the securement member is provided with a polymeric and/or biocompatible coating.

In at least one embodiment the securement member stent is constructed and arranged to deliver one or more therapeutic agents.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIG. 2 is a partial side view of a stent constructed in accordance with an embodiment of the invention.

DETAILED DESCRIPTION OF THE INVENTION

Figure 1:
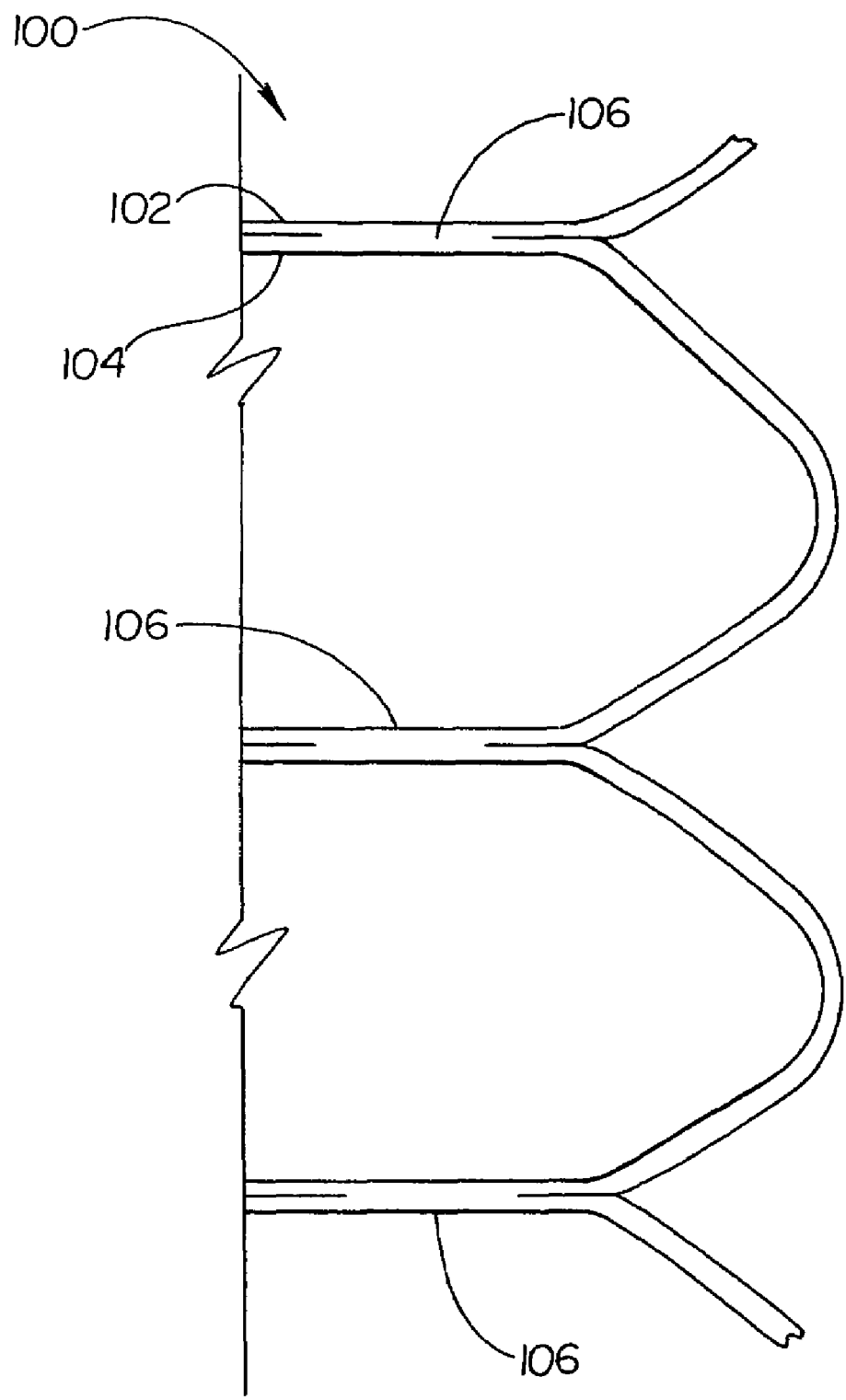
FIG. 1 is a partial side view of a PRIOR ART stent.

While this invention may be embodied in many different forms, there are described in detail herein embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The present invention is embodied in a variety of forms. In at least one embodiment, an example of which is shown in FIG. 2, the invention is directed to a stent 10 having one or more securement members 12 which provide portions of the stent that are engaged thereby with improved peel strength, improved shear or tensile strength, and/or improved radial strength over welds 106 such as are used in many prior art stents, such as the stent 100 shown in PRIOR ART FIG. 1.

As indicated above, securement members 12 may be a band or strip of suitable material that is disposed about at least two adjacent portions 14 and 16 of a stent 10 or stent member(s) 11 in order to secure or engage the adjacent portions 14 and 16 to one another. As a stent 10 may be constructed of a variety of materials, and have a variety of configurations adjacent portions 14 and 16 may be portions of one or more adjacent wires, struts, connectors, or other portions of a stent.

For example in some embodiments a stent 10 may have a region that is constructed at least partially from one or more wires and a region that is constructed from a sheet or tube that has been cut to define a plurality of struts and cell openings. The portions 14 and 16 of the stent 10 that are secured together by the securement member 12 may each be a portion or portions of one or more wires, struts, etc of either the wire region of the stent and/or the cut region of the stent. In some embodiments the stent 10 may be constructed of one or more wires wherein portions 14 and 16 of the one or more of the wires are engaged together by one or more securement members 12. As indicated by the embodiments described above the stent 10 may have any combination of desired characteristics and regions that may have portions 14 and 16 secured together by one or more securement members 12.

Figure 3A:
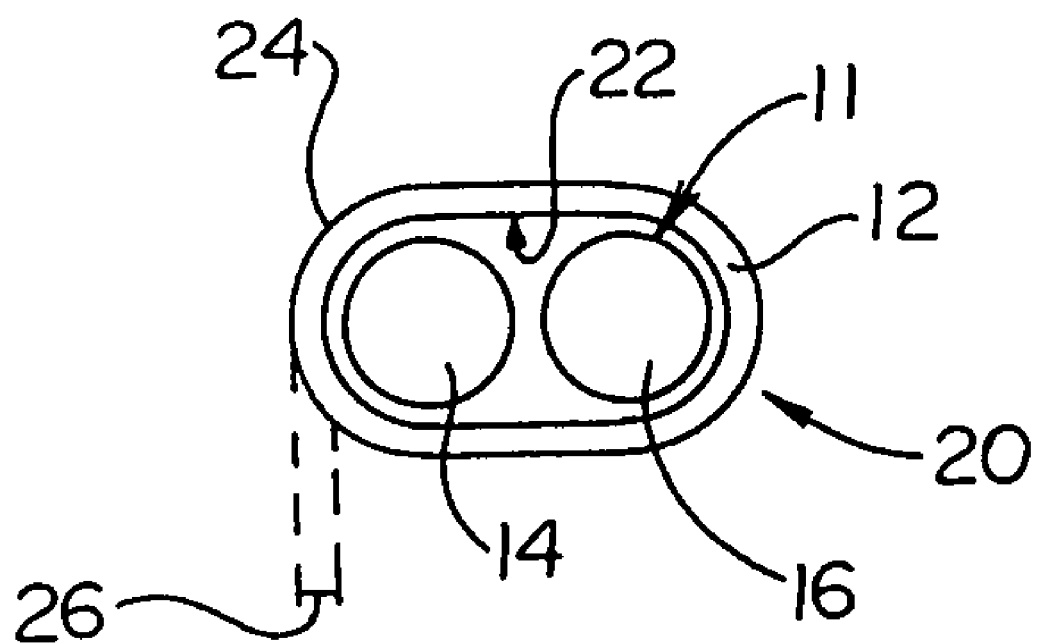
FIG. 3a is a cross-sectional view of a portion of the stent shown in FIG. 2 illustrating an embodiment of the invention wherein two adjacent portions of the stent are engaged together with a securement member.
Figure 3B:
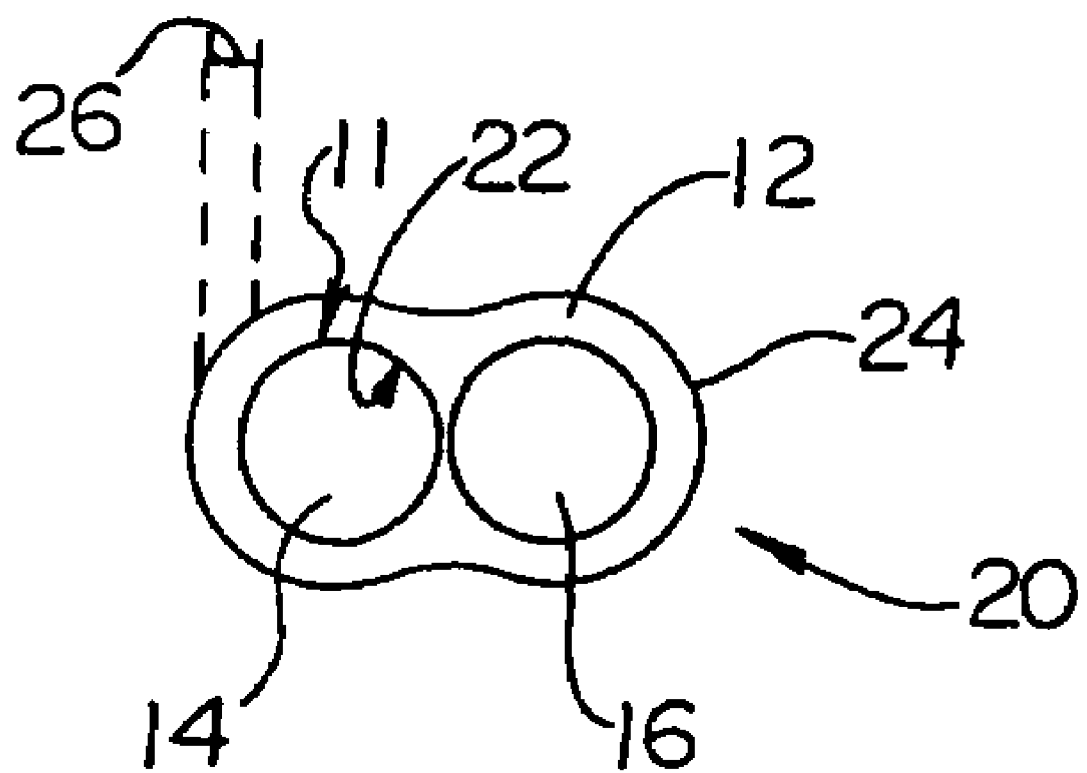
FIG. 3b is a cross-sectional view of a portion of the stent shown in FIG. 3a wherein the securement member is shown subsequent to crimping.
Figure 4:
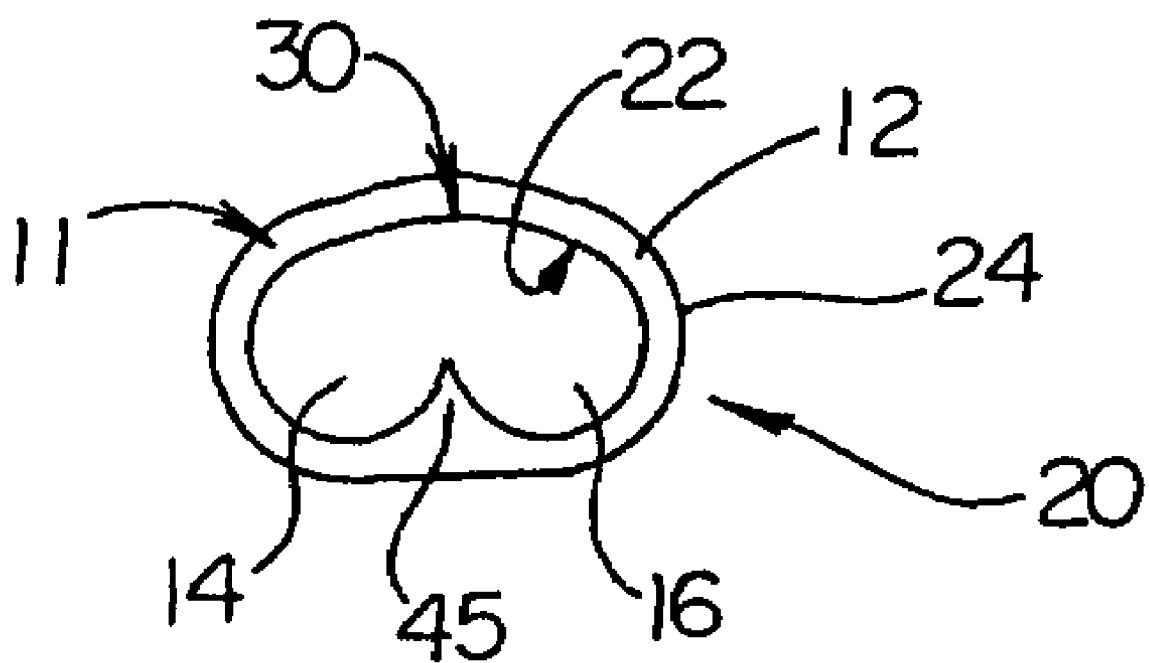
FIG. 4 is a cross-sectional view of a portion of the stent shown in FIG. 2 illustrating an embodiment of the invention.

In some embodiments, such as shown in FIGS. 2-3b a securement member 12, is a band of suitable material disposed about the adjacent portions 14 and 16 of the stent 10. In some embodiments such as is shown in FIGS. 2 and 4, a securement member 12 may be a strip of material that is wrapped around the adjacent portions 14 and 16 of the stent 12.

As is illustrated in FIGS. 3a-3b, once the securement member 12 is positioned about the adjacent portions 14 and 16, a predetermined amount of force is applied to the member 12 to crimp the member onto the stent 10 thereby fixing the member 12 on and about the adjacent portions 14 and 16. Crimping the securement member 12 reduces its inner and/or outer diameter (size) to mechanically engage the inner surface 22 of the securement member 12 to the portions 14 and 16 of the member(s) 11. Any suitable crimping tool may be used to crimp a securement member 12 into place about the adjacent portions 14 and 16 of the stent 10. Some examples of suitable crimping tools are available from Greenlee Textron Inc. of Rockford, Ill.

Once properly crimped about the adjacent portions 14 and 16 of the stent 10, the securement member 12 provides the stent with a connection region 20 having improved peal strength to resist unzipping during handling and/or use.

The improved peal strength provided by the securement member 12 over a prior art weld alone, such as is shown in PRIOR ART FIG. 1 is illustrated in the following charts:

| Sample # | Load at Max Load (lbf) |
|---|---|
| Chart 1: Stent samples having crimp member | |
| 1 | 21.64 |
| 2 | 22.47 |
| 3 | 21.07 |
| 4 | 19.40 |
| 5 | 21.29 |
| Mean | 21.17 |
| St. Dev. | 1.13 |
| Chart 2: Stent samples having prior art weld only | |
| 1 | 0.78 |
| 2 | 2.12 |
| 3 | 0.91 |
| 4 | 1.50 |
| 5 | 0.89 |
| 6 | 1.59 |
| Mean | 1.30 |
| St. Dev. | 0.53 |

Chart 1 illustrates the amount of force necessary to unzip or separate adjacent portions 14 and 16 of a stent 10 wherein the adjacent portions are secured with a securement member 12. Chart 2 illustrates the force required to unzip adjacent portions 102 and 104 of a prior art stent 100, having only a weld to secure the adjacent portions 102 and 104 together. Though the forces represented in the above charts are merely representative of a limited number of embodiments, it is nevertheless clear from a comparison of the charts, that the amount of force necessary to unzip adjacent portions of a stent 10 having a securement member 12 is substantially greater than the force required to unzip adjacent portions of a stent that are only welded together.

The physical characteristics of the member 12 may vary to a large extent. For example, a securement member 12 is comprised of a band or strip such as are respectively shown in FIGS. 3 and 4. The securement member may be constructed out of a variety of materials such as one or more metals and/or polymer materials. In some embodiments the securement member is at least partially constructed of stainless steel, nickel, titanium, gold, platinum, and combinations and/or alloys thereof. In some embodiments the securement member 12 is at least partially radiopaque. In some embodiments the securement member 12 is at least partially constructed of nitinol. In some embodiments the inner surface 22 and/or outer surface 24 of the securement member 12 is at least partially coated with one or more polymers. In some embodiments the securement member 12 is comprised of one or more layers of similar or different materials.

The dimensions of the securement member 12 may also vary greatly. In some embodiments for example the thickness, indicated at reference numeral 26 of the securement member 12 is about 0.001 inches to about 0.01 inches. In some embodiments the thickness 26 is about 0.003 (0.075 mm) to about 0.007 inches (0.18 mm). Dimensional characteristics such as length and width of the securement member 12 will depend on the number and size of the adjacent portions of the stent 10, about which the member 12 is disposed. For example, in the embodiments shown in FIGS. 3 and 4 the securement member 12 is respectively disposed about two adjacent portions 14 and 16 of the stent 10, whereas in the embodiment shown in FIG. 5 three adjacent portions 14, 16 and 18 are secured within the securement member 12. Where the caliber or thickness of the portions 14, 16 and/or 18 are the same in each embodiment, the crimping member 12 in the embodiment of FIG. 5 will be wider than the crimping member 12 in the embodiment of FIG. 3 or 4.

The various strength characteristics of the connection region 20 may be further enhanced by providing additional securement mechanism(s) between the crimping member 12 and the adjacent portions of the stent 10. Such mechanism may include additional bonds between the adjacent portions 14, 16, and/or 18, etc, such as by application of one or more adhesives, mechanical interfaces, welds, etc.

In the embodiment shown in FIGS. 2 and 4, the securement member 12 has selectively heated along the longitudinal seam between portions 14 and 16. The resulting securement assembly includes a weld region 30 wherein a portion of the adjacent portions 14 and 16 and the securement member 12 have been fused or welded together.

Figure 5:
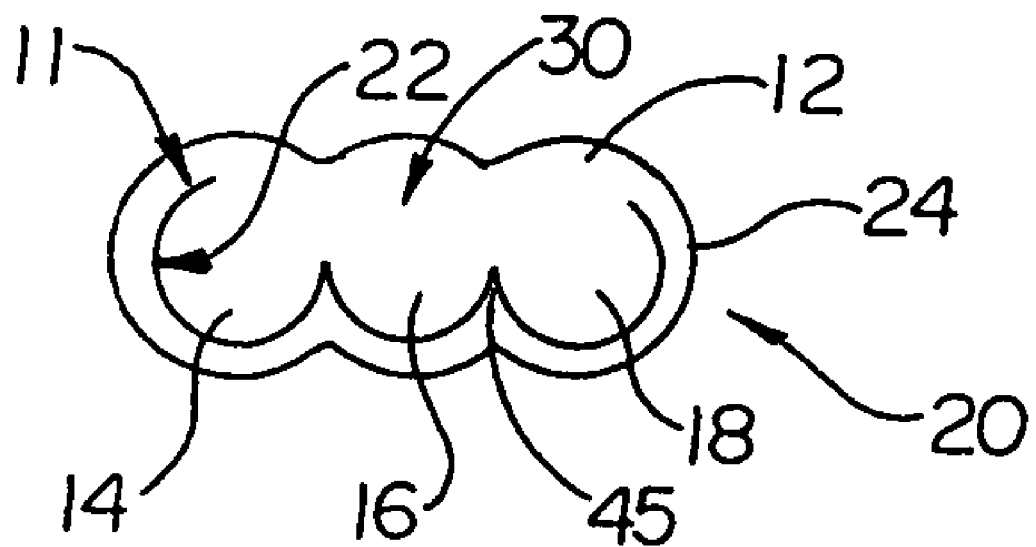
FIG. 5 is a cross-sectional view of a portion of the stent shown in FIG. 2 illustrating an embodiment of the invention.

In the embodiment shown in FIGS. 2 and 5 the upper side 32 of the securement member 12 has been heated to fuse the entire length of the adjacent portions 14, 16 and 18 to the inner surface 22 of the securement member 12. The resulting weld region 30 corresponds to the upper side 32 of the securement member 12. In an alternative embodiment shown in FIG. 6 the both the upper side 32 and the lower side 34 of the securement member 12 have been welded to the adjacent portions 14, 16 and 18 of the stent member(s) 11.

In the various embodiments of the invention, it should be noted that while heat sufficient to weld the adjacent portions of the stent to one another and/or weld one or more of the adjacent portions to the securement member may be provided to the stent in a variety of ways, in at least one embodiment a weld region 30 is formed by application of heat by laser welding or similar mechanism.

Figure 6:
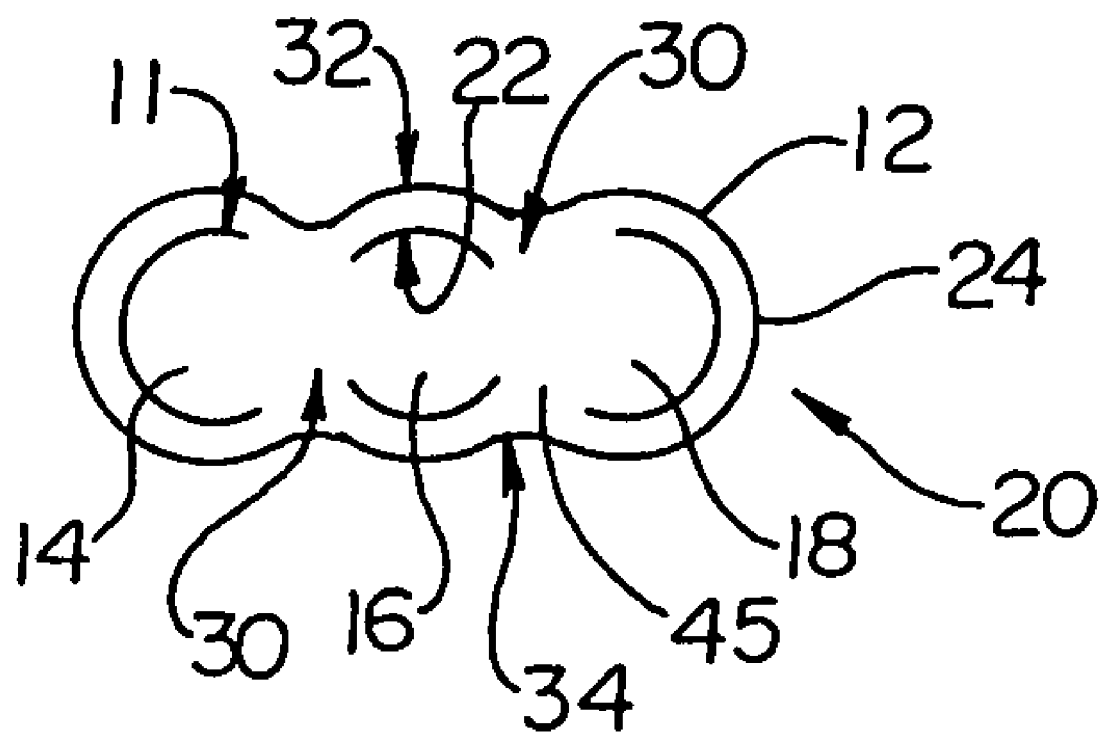
FIG. 6 is a cross-sectional view of a portion of the stent shown in FIG. 2 illustrating an embodiment of the invention.
Figure 7:
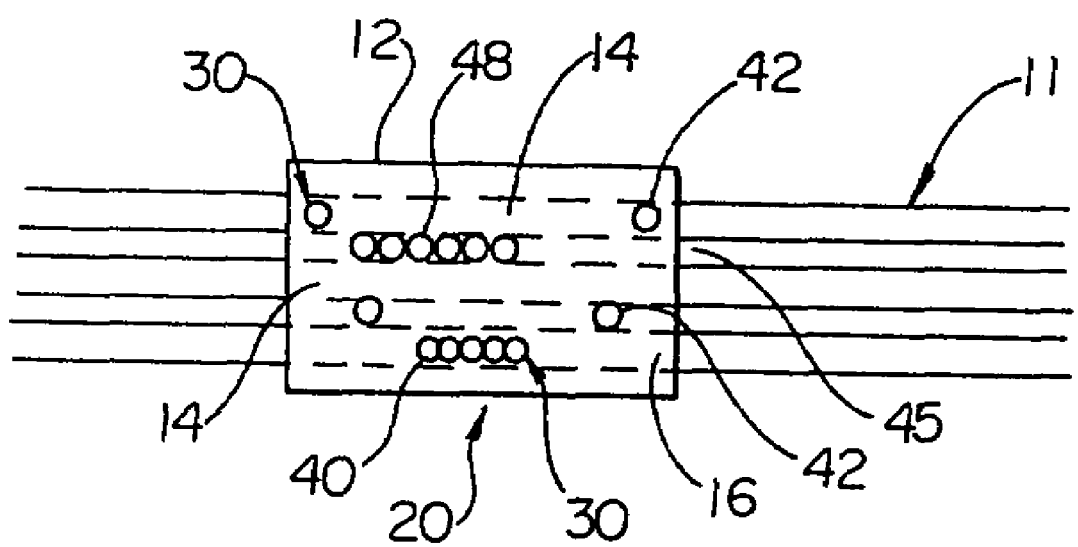
FIG. 7 is partial top-down view of a portion of a stent constructed in accordance with an embodiment of the invention.

As indicated in the examples shown in FIGS. 4-6 the size, shape and configuration of a weld region or regions 30 may be varied. In the embodiment shown in FIG. 7 for example, the securement member 12 is welded to the adjacent portions 14, 16, and 18 respectively by a variety of different configurations of weld regions 30. For example portion 14 includes a spot weld 42 at the proximal end region 44 and the distal end region 46 of the securement member 12. In another example, portion 18 includes a seam weld 48 which fuses a predetermined length of the securement member 12 and portion 18.

In some embodiments the adjacent portions 14, 16, 18, etc, may define a space or a seam 45 therebetween. In the embodiment shown in FIG. 7 a portion of the securement member 12 overlaying the seam 45 between portions 14 and 16 includes a weld region 30 in the form of a seam weld 48. The seam 45 between portions 16 and 18 includes a spot weld 42 at the proximal end region 44 and the distal end region 46 of the securement member 12.

Spot welds 42 and seam welds 48 may be utilized in a variety of configurations and patterns to provide varying degrees of engagement between the adjacent portions 14, 16, 18, etc, of the member(s) 11; and varying degrees of engagement between the member(s) 11 and the securement member 12. One or more spot welds 42 and/or seam welds 48 may be formed between one or more sections of the adjacent portions 14, 16, 18, etc, as well as between one or more sections of the adjacent portions 14, 16, 18, etc, and one or more portions of the securement member 12.

Figure 8:
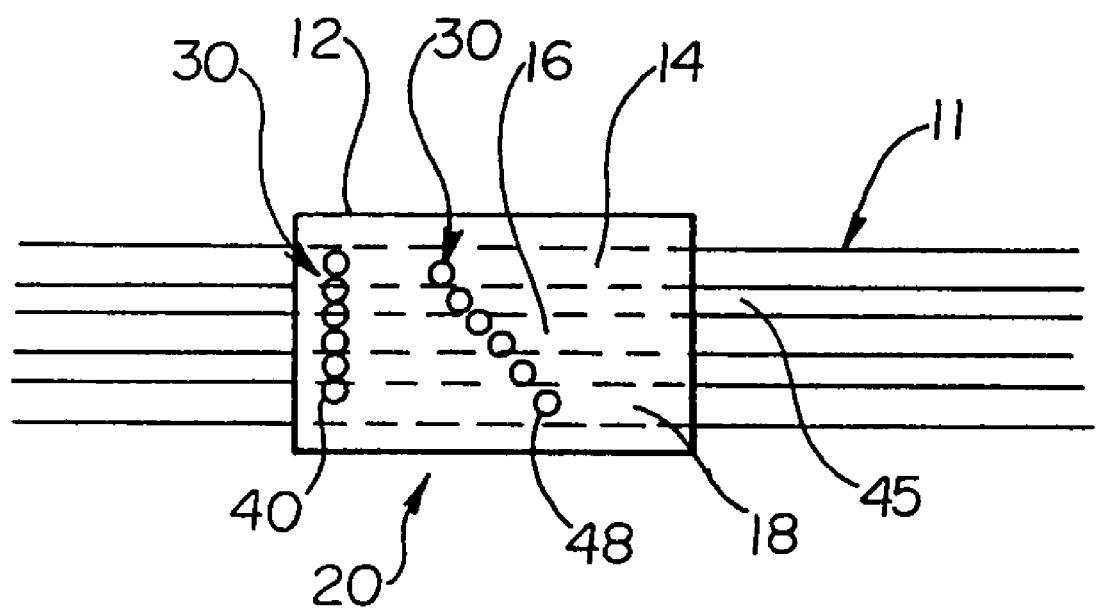
FIG. 8 is partial top-down view of a portion of a stent constructed in accordance with an embodiment of the invention.

In the embodiment shown in FIG. 8, a seam weld 48 extends laterally across the distal end region 46 of the securement member 12 to form a weld region 30 between a section of all the adjacent portions 14, 16 and 18 and between the securement member 12 and each of the adjacent portions 14, 16 and 18 of the member(s) 11.

Figure 9:
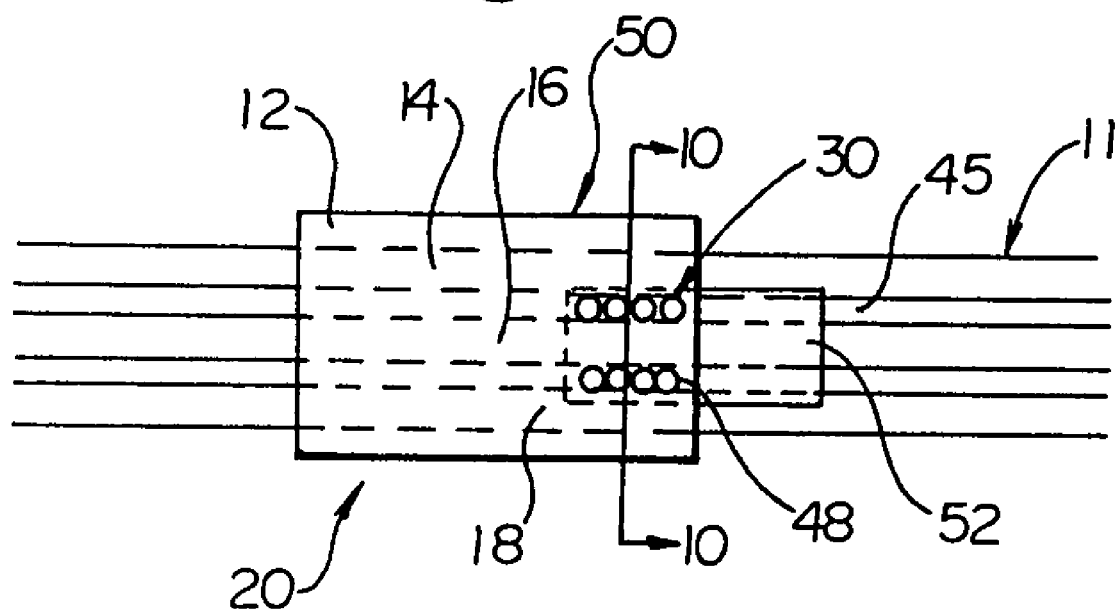
FIG. 9 is partial top-down view of a portion of a stent constructed in accordance with an embodiment of the invention.
Figure 10:
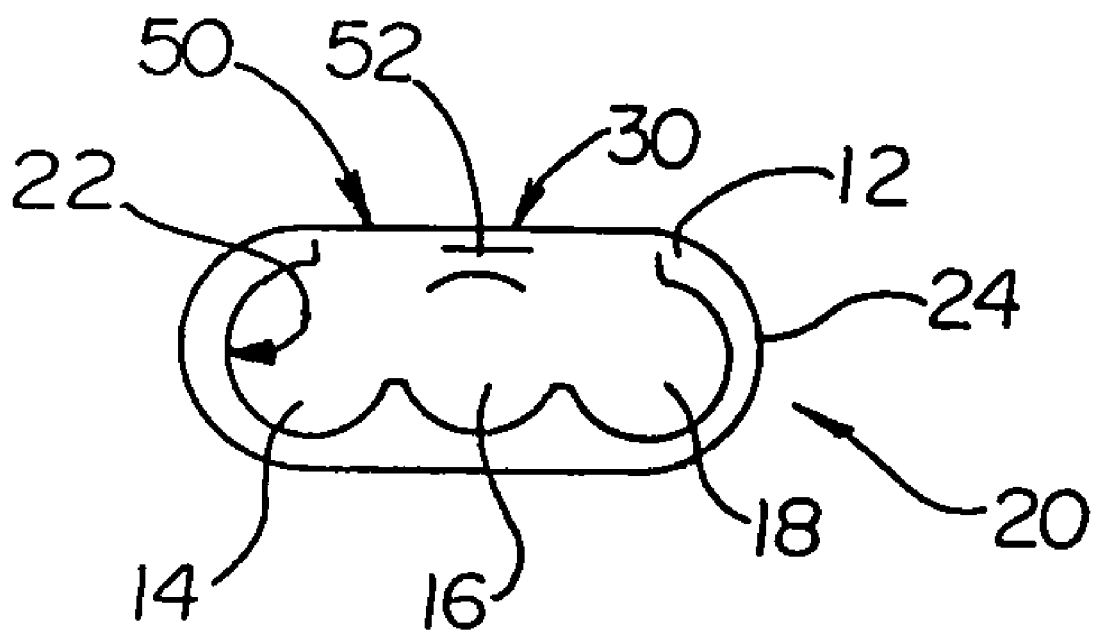
FIG. 10 is a cross-sectional view of a portion of the stent shown in FIG. 9 illustrating an embodiment of the invention.

In the various embodiments shown and described herein, the securement member 12 is a portion of a securement assembly 50. The securement assembly 50 comprises the securement member 12 and any adjacent portions 14, 16, 18, etc. secured therein, as well as any additional securement mechanisms such as weld location(s) 30. In the embodiment shown in FIGS. 9 and 10 the assembly 50 further comprises one or more strengthening members 52. A strengthening member 52 is a section of metal or other material that is positioned between the member(s) 11 and the securement member 12. In some embodiments the strengthening member 52 is sufficiently malleable so as to accommodate the bending and flexing of the stent 10 without exerting undesired leverage or pressure on the securement member 12.

The assembly 50 may include one or more strengthening members 52 at one or both ends 44 and 46 of the securement member 12. Where multiple strengthening members 52 are present, the strengthening members may be positioned on opposite or the same sides at either or both ends of the securement member 12.

A strengthening member may have any length greater than or less than the length of the securement member 12. However, in the embodiment shown the securement member 12 overlaps the strengthening member 52, by a length of at least 1 mm and at least 1 mm of the strengthening member 52 extends beyond the end region 44 or 46 of the securement member 12. In some embodiments the extent of overlap of the strengthening member 52 by the securement member 12 is at least 2 mm. In some embodiments the length of the strengthening member 52 which extends beyond the securement member 12 is at least 2 mm.

Where the assembly 50 includes one or more strengthening members, one or more weld regions 30 may be formed between the member(s) 11, the strengthening member 52, the securement member 12 and any combination thereof. In the embodiment shown in FIGS. 9 and 10 two seam welds 48 are positioned along the seams 45 between portion 14 and 16, and between portion 16 and 18. The seam welds 48 provide a fusion of material between the members 11, strengthening member 52, and the securement member 12. An assembly 50 may have any of a variety of alternative and/or additional configurations of weld locations as indicated above.

In some embodiments, a strengthening member 52 is a substantially flattened ribbon of metal such as nitinol, stainless steel, gold, platinum, etc.

In at least one embodiment a strengthening member 52 has a predetermined radiopacity. In some embodiments the radiopacity of the strengthening member is greater than or less than the radiopacity of the securement member 52 and/or the member(s) 11.

In at least one embodiment the strengthening member has a thickness, as measured between the member(s) 111 and securement member 12, of about 0.01 inches to about 0.02 inches. In some embodiments the thickness is about 0.015 inches.

In some embodiments the assembly 50, or one or more portions thereof, may be configured to deliver one or more therapeutic agents to a body location. One or more members 12 maybe configured to include one or more holes, notches, or other surface features to which one or more therapeutic agents may be placed for delivery to the aneurysm site. A therapeutic agent may be placed on the stent in the form of a coating. In at least one embodiment the coating includes at least one therapeutic agent and at least one polymer.

A therapeutic agent may be a drug, a non-genetic agent, a genetic agent, etc. Some examples of suitable non-genetic therapeutic agents include but a re not limited to: anti-thrombogenic agents such as heparin, heparin derivatives, urokinase, and PPack (dextrophenylalanine proline arginine chloromethylketone); anti-proliferative agents such as enoxaprin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine and ropivacaine; anti-coagulants such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters, vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin; bifunctional molecules consisting of an antibody and a cytotoxin; cholesterol-lowering agents; vasodilating agents; and agents which interfere with endogenous vascoactive mechanisms, and any combinations thereof.

Where an agent includes a genetic therapeutic agent, such a genetic agent may include but is not limited to: anti-sense DNA and RNA; DNA coding for anti-sense RNA, tRNA or rRNA to replace defective or deficient endogenous molecules; angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; cell cycle inhibitors including CD inhibitors, thymidine kinase ("TK") and other agents useful for interfering with cell proliferation; at least one of the family of bone morphogenic proteins ("BMP's") such as BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Any of BMP-2, BMP-3, BMP-4, BMP-5, BMP-6 and BMP-7; dimeric proteins such as homodimers, heterodimers, or combinations thereof, alone or together with other molecules; molecules capable of inducing an upstream or downstream effect of a BMP such as "hedgehog" proteins, or the DNA's encoding them and any combinations thereof.

Where a therapeutic includes cellular material, the cellular material may include but is not limited to: cells of human origin (autologous or allogeneic); cells of non-human origin (xenogeneic) and any combination thereof.

Where a therapeutic agent comprises at least one polymer coating, the at least one coating may include but is not limited to: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers such as EVA; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions such as polyurethane dispersions (BAYHDROL®, etc.), fibrin, collagen and derivatives thereof; polysaccharides such as celluloses, starches, dextrans, alginates and derivatives; hyaluronic acid; squalene emulsions; polyacrylic acid, a copolymer of polylactic acid and polycaprolactone; medical-grade biodegradable materials such as PGA-TMC, Tyrosine-Derived Polycarbonates and arylates; polycaprolactone co butyl acrylate and other co polymers; Poly-L-lactic acid blends with DL-Lactic Acid; Poly(lactic acid-co-glycolic acid); polycaprolactone co PLA; polycaprolactone co butyl acrylate and other copolymers; Tyrosine-Derived Polycarbonates and arylate; poly amino acid; polyphosphazenes; polyiminocarbonates; polydimethyltrimethylcarbonates; biodegradable CA/PO$_4$'s; cyanoacrylate; 50/50 DLPLG; polydioxanone; polypropylene fumarate; polydepsipeptides; macromolecules such as chitosan and Hydroxylpropylmethylcellulose; surface erodible material; maleic anhydride copolymers; zinc-calcium phosphate; amorphous polyanhydrides; sugar; carbohydrate; gelatin; biodegradable polymers; and polymers dissolvable in bodily fluids; and any combinations thereof.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. A stent comprising:
   a first section;
   a second section;
   at least one securement member, the at least one securement member disposed about at least one region of the first section and at least one region of the second section, the at least one securement member having an uncrimped diameter and a crimped diameter, the crimped diameter being less than the uncrimped diameter, when the at least one securement member is in the crimped diameter at least a portion of an inner surface of the at least one securement member is fixedly engaged to the at least one region of the first section and the at least one region of the second section, in the crimped diameter, the at least one region of the first section and the at least one region of the second section being adjacent to each other, wherein at least a portion of the at least one region of the first section and at least a portion of the at least one region of the second section comprise at least one weld positioned along the seam; and
   at least one separate strengthening member comprising a first portion positioned between the at least one securement member and at least one of the first section and the second section, the strengthening member also comprising a second portion extending beyond an end of the at least one securement member.

2. The stent of claim 1 wherein at least one of the first section and second section is at least partially constructed of at least one wire.

3. The stent of claim 1 wherein at least one of the first section and second section is at least partially constructed of a plurality of struts, wherein adjacent struts define at least one cell opening.

4. The stent of claim 1 wherein at least a portion of the at least one region of the first section and at least a portion of the at least one region of the second section are fused together along the seam.

5. The stent of claim 1 wherein the at least a portion of the at least one region of the first section and the at least a portion of the at least one region of the second section and the at least a portion of the inner surface of the at least one securement member comprise the at least one weld.

6. The stent of claim 1 wherein the at least one weld is positioned between the at least a portion of the inner surface of the at least one securement member and at least one portion of at least one of the at least one region of the first section and the at least one region of the second section.

7. The stent of claim 6 wherein the at least one weld is selected from the group consisting of: at least one seam weld, at least one spot weld and any combination thereof.

8. The stent of claim 1 wherein at least one of the first portion and the second portion of the at least one strengthening member has a length of about 2 mm.

9. The stent of claim 1 wherein the at least one strengthening member is a at least partially constructed of at least one metal selected from the group consisting of nitinol, stainless steel, platinum, gold and any combination thereof.

10. The stent of claim 1 wherein the at least one strengthening member is at least partially radiopaque.

11. The stent of claim 1 wherein the at least one strengthening member has a thickness, the thickness being about 0.01 inches to about 0.02 inches.

12. The stent of claim 1 wherein the at least one strengthening member has a thickness, the thickness being about 0.015 inches.

13. The stent of claim 1 wherein at least one of the first section and second section is characterized by being from the group consisting of self-expandable, balloon expandable, and hybrid expandable.

14. The stent of claim 1 wherein the first section is a balloon expandable stent body and the second section is a self-expandable stent body.

15. The stent of claim 1 wherein at least one of the first section and second section is at least partially constructed of a shape memory material.

16. The stent of claim 1 wherein at least one of the first section and second section is at least partially constructed of nitinol.

17. The stent of claim 1 wherein the at least one securement member is at least partially constructed of the group consisting of: stainless steel, nickel, titanium, gold, platinum, and any combinations thereof.

18. The stent of claim 1 wherein the at least one securement member is at least partially constructed of nitinol.

19. The stent of claim 1 wherein the at least one securement member is at least partially radiopaque.

20. The stent of claim 1 wherein the at least one securement member has a thickness the thickness being about 0.001 inches to about 0.01 inches.

21. The stent of claim 1 wherein the at least one securement member has a thickness the thickness being about 0.003 to about 0.007 inches.

22. The stent of claim 1 further comprising a third section, the at least one securement member disposed about the at least one region of the first section, the at least one region of the second section, and at least one region of the third section, when the at least one securement member is in the crimped diameter the at least a portion of the inner surface of the at least one securement member is fixedly engaged to the at least one region of the first section, the at least one region of the second section and the at least one region of the third section.

23. The stent of claim 1 wherein at least a portion of the stent is coated with at least one therapeutic agent.

24. The stent of claim 23 wherein the at least a portion of the stent is at least a portion of the at least one securement member.

25. The stent of claim 23 wherein the at least one therapeutic agent is at least one therapeutic agent selected from the group consisting of: anti-thrombogenic agents; anti-proliferative agents; anti-inflammatory agents;
   antineoplastic/antiproliferative/anti-miotic agents; anesthetic agents; anti-coagulants; vascular cell growth promoters; vascular cell growth inhibitors; bifunctional molecules consisting of an antibody and a cytotoxin; cholesterol-lowering agents; vasodilating agents; and agents which interfere with endogenous vasoactive mechanisms, and any combinations thereof.

26. The stent of claim 25 wherein the anti-thrombogenic agents are selected from the group consisting of heparin, heparin derivatives, urokinase, and PPack (dextrophenylalanine proline arginine chloromethylketone).

27. The stent of claim 25 wherein the anti-proliferative agents are selected from the group consisting of enoxaprin, angiopeptin, monoclonal antibodies capable of blocking smooth muscle cell proliferation, hirudin, and acetylsalicylic acid.

28. The stent of claim 25 wherein the anti-inflammatory agents are selected from the group consisting of dexamethasone, prednisolone, corticosterone, budesonide, estrogen, sulfasalazine, and mesalamine.

29. The stent of claim 25 wherein the antineoplastic/antiproliferative/anti-miotic agents are selected from the group consisting of paclitaxel, 5-fluorouracil, cisplatin, vinblastine, vincristine, epothilones, endostatin, angiostatin and thymidine kinase inhibitors.

30. The stent of claim 25 wherein the anesthetic agents are selected from the group consisting of lidocaine, bupivacaine and ropivacaine.

31. The stent of claim 25 wherein the anti-coagulants are selected from the group consisting of D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides.

32. The stent of claim 25 wherein the vascular cell growth promoters are selected from the group consisting of growth factor inhibitors, growth factor receptor antagonists, transcriptional activators, and translational promoters.

33. The stent of claim 25 wherein the vascular cell growth inhibitors are selected from the group consisting of growth factor inhibitors, growth factor receptor antagonists, transcriptional repressors, translational repressors, replication inhibitors, inhibitory antibodies, antibodies directed against growth factors, and bifunctional molecules consisting of a growth factor and a cytotoxin.

34. The stent of claim 23 wherein the at least one therapeutic agent is at least one therapeutic agent selected from the group consisting of: anti-sense DNA and RNA; DNA coding for anti-sense RNA, tRNA or rRNA to replace defective or deficient endogenous molecules; angiogenic factors including growth factors; cell cycle inhibitors; at least one of the family of bone morphogenic proteins ("BMP's"); dimeric proteins ; molecules capable of inducing an upstream or downstream effect of a BMP ; and any combinations thereof.

35. The stent of claim 34 wherein the growth factors are selected from the group consisting of acidic and basic fibroblast growth factors, vascular endothelial growth factors, epidermal growth factors, transforming growth factors .alpha. and .beta., platelet-derived endothelial growth factors, platelet-derived growth factors, tumor necrosis factors .alpha., hepatocyte growth factors, and insulin like growth factors.

36. The stent of claim 34 wherein the cell cycle inhibitors are selected from the group consisting of CD inhibitors, thymidine kinase ("TK") and other agents useful for interfering with cell proliferation.

37. The stent of claim 34 wherein the bone morphogenic proteins are selected from the group consisting of BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16.

38. The stent of claim 34 wherein the molecules capable of inducing an upstream or downstream effect of a BMP are selected from the group consisting of "hedgehog" proteins, and the DNA's encoding "hedgehog" proteins.

39. The stent of claim 23 wherein the at least one therapeutic agent is at least one type of cellular material selected from the group consisting of: cells of human origin; cells of non-human origin ; and any combination thereof.

40. The stent of claim 23 wherein the at least one therapeutic agent comprises at least one polymer coating, the at least one coating selected from the group consisting of: polycarboxylic acids; cellulosic polymers, including cellulose acetate and cellulose nitrate; gelatin; polyvinylpyrrolidone; cross-linked polyvinylpyrrolidone; polyanhydrides including maleic anhydride polymers; polyamides; polyvinyl alcohols; copolymers of vinyl monomers; polyvinyl ethers; polyvinyl aromatics; polyethylene oxides; glycosaminoglycans; polysaccharides; polyesters including polyethylene terephthalate; polyacrylamides; polyethers; polyether sulfone; polycarbonate; polyalkylenes including polypropylene, polyethylene and high molecular weight polyethylene; halogenated polyalkylenes including polytetrafluoroethylene; polyurethanes; polyorthoesters; proteins; polypeptides; silicones; siloxane polymers; polylactic acid; polyglycolic acid; polycaprolactone; polyhydroxybutyrate valerate and blends and copolymers thereof; coatings from polymer dispersions; polysaccharides; hyaluronic acid;

squalene emulsions; polyacrylic acid, a copolymer of polylactic acid and polycaprolactone;

medical-grade biodegradable materials; polycaprolactone co butyl acrylate and other co polymers; Poly-L-lactic acid blends with DL-Lactic Acid; Poly(lactic acid-co-glycolic acid);

polycaprolactone co PLA; polycaprolactone co butyl acrylate and other copolymers; Tyrosine-Derived Polycarbonates and arylate; poly amino acid; polyphosphazenes; polyiminocarbonates;

polydimethyltrimethylcarbonates; biodegradable CA/PO sub 4's; cyanoacrylate; 50/50 DLPLG;

polydioxanone; polypropylene fumarate; polydepsipeptides; macromolecules; surface erodible material; maleic anhydride copolymers; zinc-calcium phosphate; amorphous polyanhydrides;

sugar; carbohydrate; gelatin; biodegradable polymers; and polymers dissolvable in bodily fluids; and any combinations thereof.

41. The stent of claim 40 wherein the coatings from polymer dispersions are selected from the group consisting of polyurethane dispersions, fibrin, collagen and derivatives thereof.

42. The stent of claim 40 wherein the polysaccharides are selected from the group consisting of celluloses, starches, dextrans, alginates and derivatives.

43. The stent of claim 40 wherein the medical-grade biodegradable materials are selected from the group consisting of PGA-TMC, Tyrosine-Derived Polycarbonates and arylates.

44. The stent of claim 40 wherein the macromolecules are selected from the group consisting of chitosan and Hydroxylpropylmethylcellulose.

45. A stent comprising:
a first section;
a second section;
at least one securement member, the at least one securement member disposed about at least one region of the first section and at least one region of the second section, the at least one securement member having an uncrimped diameter and a crimped diameter, the crimped diameter being less than the uncrimped diameter, when the at least one securement member is in the crimped diameter at least a portion of an inner surface of the at least one securement member is fixedly engaged to the at least one region of the first section and the at least one region of the second section, in the crimped diameter the at least one region of the first section and the at least one region of the second section being immediately adjacent one another, the at least one securement member further comprising a longitudinal seam at least partially separating the at least one region of the first section and the at least one region of the second section from each other;
at least one separate strengthening member comprising a first portion positioned between the at least one securement member and at least one of the first section and the second section, the strengthening member also comprising a second portion extending beyond an end of the at least one securement member; and
at least one weld positioned along the seam, the at least one weld securing the at least one separate strengthening member to the at least one securement member.

46. The stent of claim 45 wherein the at least one weld is positioned between the at least a portion of the inner surface of the at least one securement member, the at least one portion of at least one of the at least one region of the first section and the at least one region of the second section, and the at least a portion of the at least one strengthening member.

47. A stent comprising:
a first section;
a second section
a securement member disposed about the first section and the second section, wherein an inner surface of the securement member is fixedly engaged to the first section and the second section, wherein the securement member comprises a longitudinal seam at least partially separating the first section and the second section from each other;
a weld positioned along the seam; and
at least one separate strengthening member comprising a first portion positioned between the securement member and at least one of the first section and the second section, the strenghthening member also comprising a second portion extending beyond an end of the securement member.

48. The stent according to claim 47, comprising a plurality of securement members.

49. The stent according to claim 47, comprising a plurality of welds.

* * * * *